United States Patent [19]

Goudfrooy

[11] 4,299,212
[45] Nov. 10, 1981

[54] EXTERNAL FRACTURE IMMOBILIZATION SPLINT

[75] Inventor: Hendrik Goudfrooy, Amsterdam, Netherlands

[73] Assignee: Nederlandsch Central Organisatie voor Toegepast-Natuurwetenschappelijk Onderzoek, The Hague, Netherlands

[21] Appl. No.: 940,276

[22] Filed: Sep. 7, 1978

[30] Foreign Application Priority Data

Sep. 8, 1977 [NL] Netherlands .......................... 7709897

[51] Int. Cl.³ ................................................ A61F 5/04
[52] U.S. Cl. .............................. 128/92 A; 128/92 EB
[58] Field of Search ................. 128/92 R, 92 A, 92 E, 128/92 EB

[56] References Cited

U.S. PATENT DOCUMENTS

| | | | |
|---|---|---|---|
| 902,040 | 10/1908 | Wyckoff | 128/92 E |
| 2,251,209 | 7/1941 | Stader | 128/92 A |
| 2,346,346 | 4/1944 | Anderson | 128/92 A |
| 2,391,537 | 12/1945 | Anderson | 128/92 A |
| 2,391,693 | 12/1945 | Ettinger | 128/92 A |
| 2,393,694 | 1/1946 | Kirschner | 128/92 A |
| 3,128,768 | 4/1964 | Geistauts | 128/92 E |
| 4,135,505 | 1/1979 | Day | 128/92 A |

FOREIGN PATENT DOCUMENTS

| | | | |
|---|---|---|---|
| 789882 | 11/1935 | France | 128/92 A |
| 203544 | 6/1939 | Switzerland . | |
| 303453 | 2/1955 | Switzerland . | |
| 397202 | 1/1974 | U.S.S.R. | 128/92 A |
| 578958 | 11/1977 | U.S.S.R. | 128/92 R |

Primary Examiner—Robert W. Michell
Assistant Examiner—C. W. Shedd
Attorney, Agent, or Firm—Hammond & Littell, Weissenberger and Muserlian

[57] ABSTRACT

This invention is directed to an external fracture immobilization splint for fractured bones comprising a connecting rod and two clamping heads, wherein each clamping head slidably holds at a mutual angle two or more bone pins, and comprises two parts, each of which contains a guide opening for each bone pin held by the clamping head, said parts being mutually movable in a direction at an angle to the length of the bone pins, an immobilization member being arranged between said parts of the clamping head to move said parts mutually, said bone pins limiting said movement of said parts of the clamping head by contacting the walls of said guide openings and thus being simultaneously secured in the clamping head, the guide openings for the bone pins being arranged so that, when viewed along the axis of the clamping head vertical to the fractured bone, each of the bone pins appears tangential to a mutually connecting circle in a plane perpendicular to the vertical axis.

11 Claims, 5 Drawing Figures

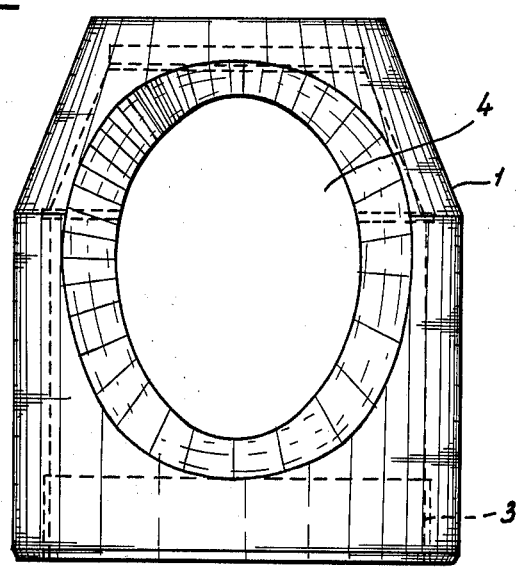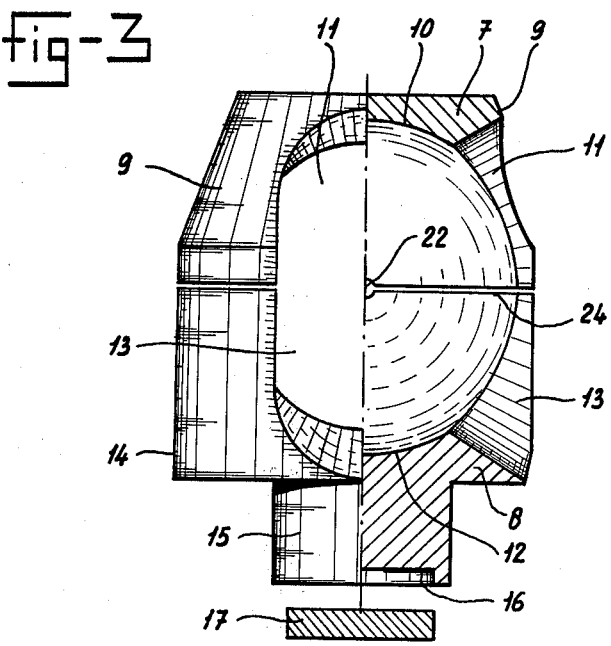

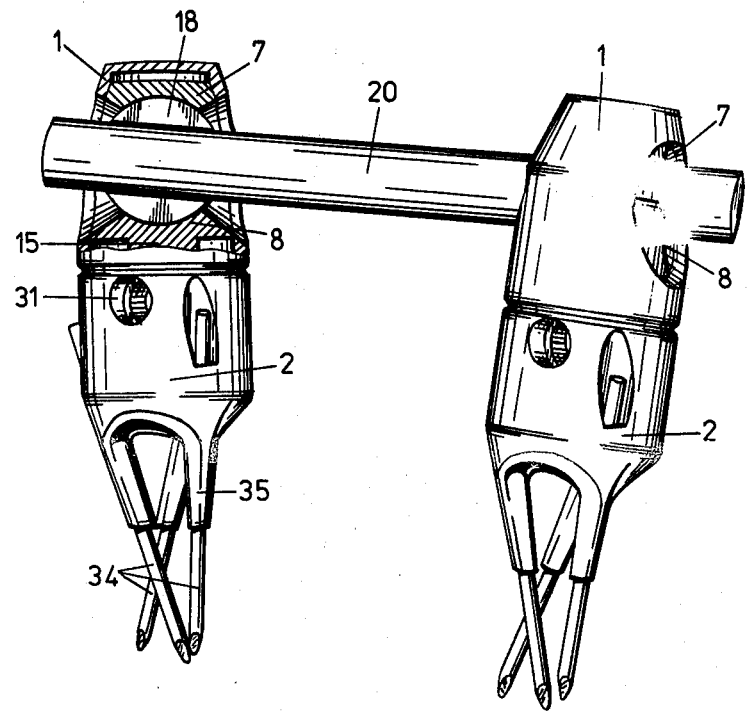

EXTERNAL FRACTURE IMMOBILIZATION SPLINT

This invention relates to an external fracture immobilisation splint for fractured bones, with pins to be introduced into the bone, secured to an external supporting structure adapted to connect the bone parts to both sides of the fracture mutually in that it includes a connecting rod and two clamping heads for the pins connected to said rod, at least two pins at a mutual angle being taken up slidably in openings in a clamping head of the splint. Splints of this type are known e.g. from Swiss Pat. No. 203,544 and from U.S. Pat. No. 2,346,346.

Such known structures require separate movements to immobilize the several parts mutually and with respect to the bone of the patient. In Swiss Pat. No. 303,453 a row of parallel pins may be immobilized simultaneously, but this needs tightening of two screws, and the parallel position of the pins is not preferred.

In the interest of the patient it is very important that there is a plurality of pins in the correct positions and that these are rapidly operable, with the least possible movement and the lowest possible forces. It is also very important that all ipossible adjustments of parts mutually and with respect to the bone are possible rapidly and accurately, with the minimum of time needed, and that the splint is as light and small as possible, without protruding parts.

In view of these objects, a splint as given in the preamble is according to the invention characterized in that for each pin in each head a guiding opening is provided in each of two parts of such a clamping head, said parts being mutually movable in a direction at an angle to the length of the pins, a single immobilization member being provided acting between said two parts of such clamping head and operable so as to move such parts of the clamping head mutually, said pins limiting said movement of said parts of the clamping head by contacting the walls of said guiding openings and being thus secured in their clamping head simultaneously.

This allows a rapid immobilization of the pins of one head by operating one part only and with the least possible risk of undesired forces on the bone.

Preferably, the splint according to the invention is further characterized in that the immobilization member is also in contact with clamping means in its clamping head so as to move them simultaneously with the movement thereby of the said two parts acting on the pins to clamp the clamping head to a rod of the external supporting structure simultaneously with the clamping of the pins.

This causes the same movement for operation of the immobilization member both to secure the pins and to secure the head with the pins to the connecting rod.

As stated, there are at least two pins at an angle in each head. It has appeared most preferable to apply three pins per head at an angle to each other, and although these may take up different positions the most preferred arrangement according to the invention is one in which the guiding openings for the pins in each clamping head cross each other and cross the axis of the clamping head at a distance while converging in the head towards the bone to be immobilized.

The correct position and mutual angles of the pins make smooth pins give a maximum immobilization and safe keeping of both bone parts in the correct mutual positions at the fracture in all directions. As said, the pins should not be parallel, but they should neither contact each other or come too close in the bone, but leave a free zone between them in the bone. In view thereof the invention proposes to give the three pins in each head a position so as to leave a free circle of a diameter of 8 mm in the area of their closest proximity.

Further details will become apparent in the following description of a preferred embodiment of a splint according to the invention shown in the annexed drawings.

In these drawings:

FIG. 2 shows an elevation of the top part of the casing thereof;

FIG. 3 shows in the right part an axial section and in the left part an elevation of the parts filling this top part of the casing of FIG. 2, the elevation in the left part being at an angle of 90° to the section in the right part;

FIG. 5 shows an apparatus of the invention wherein the right-hand clamping head is seen from the outside and the left-hand clamping head is seen in vertical section, through the axis, in the top portion.

All of FIGS. 1 to 4 are at an enlarged scale of about twice the real dimensions of the parts shown.

Figure 1:
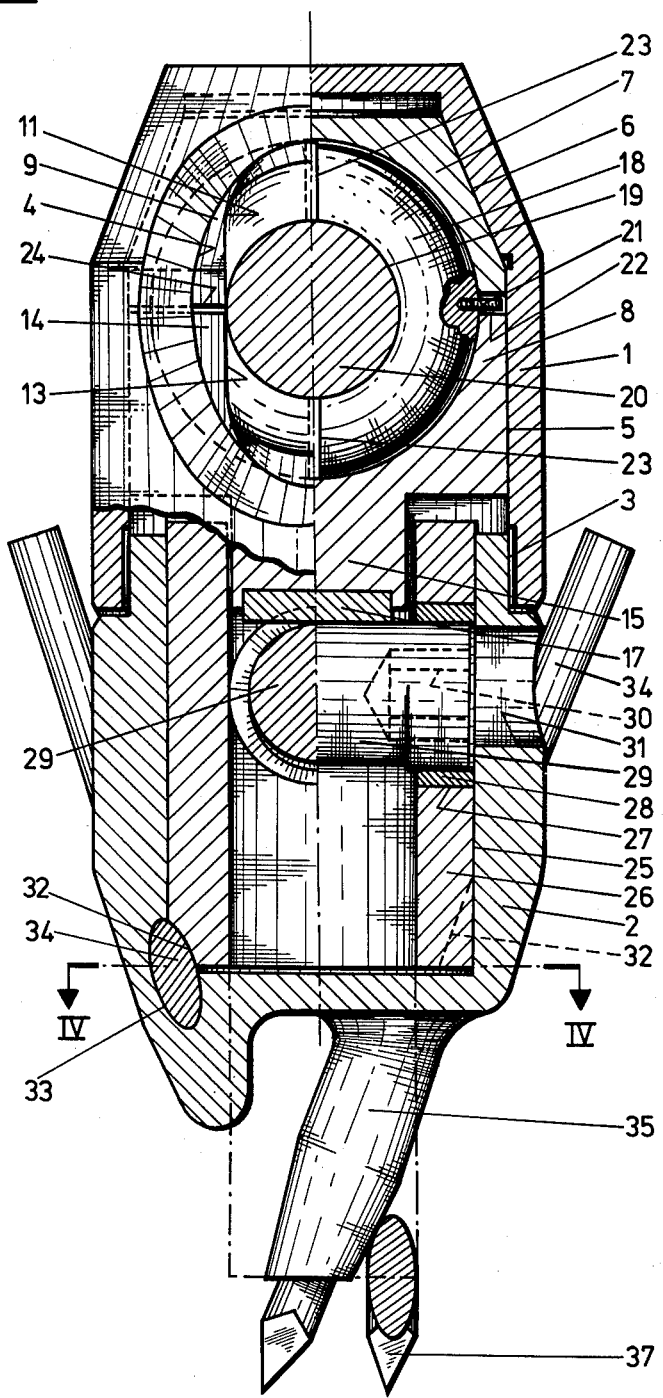
FIG. 1 shows an axial section through one of the immobilization heads of a splint in a preferred embodiment of the invention.

The head of FIG. 1 has a casing in two parts 1 and 2, connected at 3 by a screw-threaded connection. The top casing part 1 has two opposite openings 4 and an interior, which is cylindrical at 5 and conical at 6. In top casing part 1 fit two clamping parts 7 and 8 (FIG. 3). Part 7 has a conical exterior 9 over the greater part of its length, a semi-spherical interior cavity 10 and two opposite holes 11. Part 8 has a complementary semi-spherical interior cavity 12, two opposite holes 13 and a cylindrical exterior 14, with a downwardly protruding narrower cylindrical part 15, having in its lower face a recess 16 for taking up a hard disc 17 shown below it separately in FIG. 3.

Within the spherical cavity formed by the two cavities 10 and 12 there are two parts 18, each having a semi-spherical exterior surface and a semi-cylindrical inner recess 19, so that these parts 18 together form a spherical body with internal cylindrical through-going recess, adapted to take up a connector rod 20 connecting two of such heads one to each side of the fracture.

A screw 21 (FIG. 1) extends from each part 18 into suitable recesses 22 in the clamping parts 7 and 8 (FIG. 3) to allow rotation of parts 18 about a horizontal axis in the plane of drawing of FIG. 1 within the clamping parts 7 and 8, but to avoid other mutual movements. There may also be a vertical pin in recesses in the bordering faces of parts 18, e.g. in one of the zones 23 in FIG. 1, to make sure that the internal semi-cylindrical recesses 19 therein maintain the correct mutual positions.

The clamping parts 7 and 8 in operation do not contact each other, but keep a short distance as indicated at 24 in FIG. 3, and the spherical parts 18 keep a short distance as indicated at 23 in FIG. 1. This allows clamping of parts 7 and 8 onto parts 18 and clamping of parts 18 onto rod 20.

The lower casing part 2 has a central cylindrical recess 25, in which a cylindrical hollow sleeve 26 is taken up, having two opposite bores 27 with low friction lining sleeves 28 in them, to take up rotatably an eccentric pin 29, shown in elevation with its axis in the plane of the drawing in the right part of FIG. 1 and in section perpendicular to its axis in the left part thereof. The eccentric pin 29 has a hexagonal recess 30 for operation by a simple tool with a hexagonal head fitting therein to be rotated. This tool may enter through a bore 31 in casing part 2. It may be a usual tool as used for driving socket screws.

The sleeve 26 at its lower end has three inclined recessed parts 32, casing part 2 has three bores 33 for taking up transfixation pins 34 to be fixed in the human bone in holes to be drilled therein. These bores intersect the recess 25 in casing part 2 so as to open therein to one side over a short part of their lengths intermediate their ends. The recessed parts 32 have a cylindrical wall of the same radius as the pins 34 and the bores 33. Thus, if sleeve 26 is moved downward with the pins 34 present in the bores 33, this sleeve clamps the pins in place to immobilize the head of FIG. 1 with respect to these pins and thus with respect to the human bone to one side of the fracture.

Figure 4:
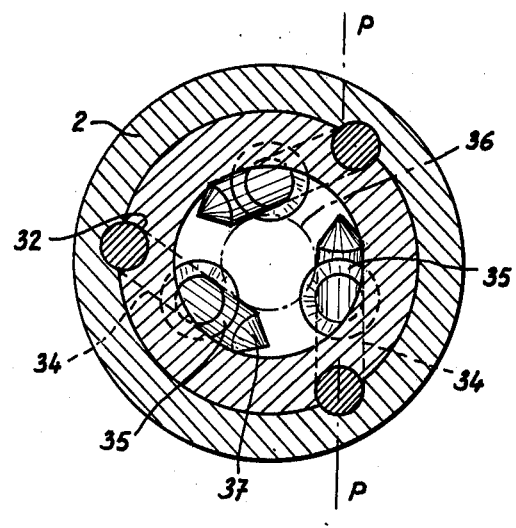
FIG. 4 shows a view, partly section, in the staggered plane indicated by IV—IV in FIG. 1.

Although one bore 33 with its pin 34 is shown in FIG. 1 as lying entirely in the plane of the drawing being a plane through the vertical axis of the head, the position of these pins and bores is different. They in fact make an angle to the plane of the drawing, so that the pins, if moved downward with respect to the position shown and the axes of the bores, do not intersect each other. This is explained with reference to FIG. 4 showing in one plane the situation at the two levels according to sections IV—IV of FIG. 1. The lower part of casing part 2 is formed by three separate sleeves 35, each one surrounding one of the pins 34, and in FIG. 4 the the reference numerals 35 indicate these sleeves at their lower ends. It will thus be clear that the pins may pass each other at some distance, leaving at their closest proximity a free circle 36 with a radius of 4 mm. In a plane parallel to the axis of the head through each pin, such pin preferably makes an angle of 17° to 21° with the direction of said axis. FIG. 1 shows the pins in a position not yet fully introduced into the bone and FIG. 4 shows them about in the final position taken up in the bone.

The head as shown is connected to a rod 20 carrying two such heads, one to each side of the bone fracture (see FIG. 5). Each head may be adjusted to the correct position by the following adjustments. The casing 1, 2 may be rotated about clamping parts 7 and 8 around the vertical axis of FIG. 1, the holes 4 (FIG. 2) allowing such movement with respect to rod 20. The head may moreover be tilted in the plane of FIG. 1 about rod 20. Furthermore, the spherical parts in the cavities 10 and 12 allow tilting of the head about a horizontal axis in the plane of drawing of FIG. 1 through rod 20, the holes 11 and 13 being made to allow for this adjustment. In this way, the head constituted by the parts of FIG. 1 may be adjusted to any desired position and in all desired directions, including a sliding of the head in longitudinal direction on the rod 20.

In the adjusted position, the eccentric pin 29 may be rotated to fix the adjusted parts. In doing this, it will push disc 17 and thus parts 7 and 8 upward and simultaneously it will, through sleeves 28 supporting this pin rotatably, push sleeves 26 downward. This will make parts 7 and 8 be moved somewhat towards each other to clamp parts 18 around rod 20 and to clamp themselves around parts 18 so as to clamp part 7 in casing part 1 along conical surface 6. All the adjustments are thus immobilized.

If in this stage no pins 34 are present, sleeve 26 will be fixed onto the bottom of recess 25. For drilling holes in the bone to take up the pins 34 the casing may be used as a jig for guiding the drill through the bores 33. The pins are then introduced through these bores into the bone. In fact, the pins themselves, having a sharp chisel-like point 37, may be used as drills.

When introducing the pins, the eccentric pin 29 should be in the loosened position after which rotation thereof to the clamping position will move sleeve 26 downward to clamp the walls of the recesses 32 thereof onto the pins after they have thus been introduced into the bone. Of course in this position the pins 34 protrude further downward than shown in FIG. 1.

It is thus possible to first adjust both heads on the bone, preferably after making incisions in skin and flesh to have the heads rest with the three free ends of the sleeves 35 immediately onto and in contact with the bone. The pins are then introduced after or together with the drilling of the holes and they may penetrate entirely through the bone and protrude therefrom by say 3 or 4 mm at the opposite end. The rod 20 is then introduced into the heads and the eccentric pin 29 is then rotated to clamp all the parts in place after proper adjustments have been made to have the bone parts in the correct mutual position and to avoid torsions and other undesired or too high forces on the bones and on the fracture.

The rod 20 may be introduced in an earlier stage or dummy-pins may be used in each head to be connected to the rod 20 in a later stage and to be pushed out of the heads by this rod.

Preferably the rod 20 and the pins 34 are chosen with such a length that there is the least possible protrusion of parts from the heads. It should be noted that the pins 34 depicted in FIG. 5 are shown as taken up in the bone and are thus farther down than in FIG. 1.

I claim:

1. An external fracture immobilization splint for use in association with two sets of bone pins respectively located on opposite sides of a fracture, said immobilization splint comprising a connecting rod and two clamping heads, each of which clamping heads slidably holds at a mutual angle two or more of said bone pins in guide openings so that the axes of the bone pins do not intersect each other, wherein each clamping head has a hollow rigid casing, a transverse opening near one end of said casing for the passage of said connecting rod to connect to the other clamping head, said transverse opening being in communication with an internal cavity in the casing, said guide openings for said bone pins opening in said cavity to cause said pins to protrude partly into said cavity, clamping means within said casing in said internal cavity comprising two clamp parts slidable therein and a clamp actuating member engaging said clamp parts, said clamp actuating member being operable when actuated to move said clamp parts in said cavity to have one clamp part clamp said rod in any desired relative position with respect to the clamping head and the other clamp part to clamp said bone pins to the casing and to engage said other clamp part with the parts of the bone pins protruding into said cavity and thereby immobilize the bone pins relative to the head and the head relative to the connecting rod simultaneously, deactuating said clamp actuating member loosening these parts simultaneously so that said splint may be adjusted or removed.

2. The immobilization splint of claim 1, wherein each clamping head holds three bone pins.

3. The immobilization splint of claim 1, wherein one of the slidable clamp parts has two bores in opposite parts of its walls to accommodate the clamp actuating member rotatably and the slidable clamp parts contact the clamp actuating member within the casing so that rotation of the clamp actuating member tends to move one slidable clamp part in one direction and the other slidable clamp part in the opposite direction.

4. The immobilization splint of claim 1, wherein at a point at which the pins protrude from the casing, the casing branches into separate thin-walled sleeves, each surrounding a pin, with a free space between such sleeves.

5. The immobilization splint of claim 1, wherein the clamp actuating member is rotatably supported by one of said two clamp parts in said cavity and is movable with respect to said one clamp part when actuated to urge said two clamp parts in opposite directions to immobilize the bone pins relative to the head and the head relative to the connecting rod simultaneously.

6. The immobilization splint of claim 1, wherein each clamping head comprises split clamping parts in the rigid casing adapted to clamp the rod in the casing in an adjustable position, a part in and slidable with respect to the casing adapted to contact the pins within the casing, and a clamp actuating member operable to move the split clamping parts in a given direction and to slide in the opposite direction the part slidable in the casing into contact with the pins and thereby immobilize the head on the connecting rod and the pins in the head simultaneously, said actuating member also being operable to loosen the respective parts simultaneously thereby mobilizing the head and the pins.

7. The immobilization splint of claim 6, wherein the split clamping parts include first parts split in one plane and further parts within said first parts split in a plane perpendicularly thereto, said parts when not immobilized being rotatable in the casing about one axis and the further parts being rotatable within said first parts about an axis perpendicular to said one axis, the casing and the first split clamping parts having openings wider than the thickness of the connecting rod to allow adjusting movements of the clamping head with respect to the rod.

8. The immobilization splint of claim 6, wherein the part slidable in the casing to immobilize the pins is a sleeve having recesses each adapted to fit around and clamp a pin in the casing.

9. The immobilization splint of claims 8 or 1, wherein the clamp actuating member is an eccentric pin rotatable to move said clamp parts.

10. The immobilization splint of claim 9 wherein each casing of said two clamping heads has at least one opening, each of said openings being arranged so as to facilitate introduction of a tool to rotate the eccentric pin.

11. The immobilization splint of claim 1, wherein the bone pins limit the movements of the parts of the clamping head inasmuch as the pins are clamped between one of the slidable parts and the walls of the guide openings and are thus simultaneously secured in the clamping head, the guide openings for the bone pins being arranged so that, when viewed along an axis coincident to the direction of sliding of clamp parts in the cavity, each of the bone pins appears tangential to an inscribed circle, which circle is centered on and perpendicular to said axis.

* * * * *

UNITED STATES PATENT AND TRADEMARK OFFICE
CERTIFICATE OF CORRECTION

PATENT NO. : 4,299,212
DATED : November 10, 1982
INVENTOR(S) : HENDRIK GOUDFROOY It is certified that error appears in the above—identified patent and that said Letters Patent is hereby corrected as shown below:

Preamble page [73]: "Nederlandsch" should read

-- Nederlandse --.

Column 1, line 26: "ipossible" should read -- possible --.

Signed and Sealed this

Thirteenth Day of April 1982

|SEAL|

*Attest:*

*Attesting Officer*

GERALD J. MOSSINGHOFF
*Commissioner of Patents and Trademarks*